United States Patent [19]
Hagiwara et al.

[11] Patent Number: 5,337,140
[45] Date of Patent: Aug. 9, 1994

[54] OPTICAL DETECTING SYSTEM WITH SELF-CORRECTION

[75] Inventors: Takashi Hagiwara; Toyoki Kanzaki; Dainichiro Kinoshita, all of Kyoto, Japan

[73] Assignee: Horiba, Ltd., Kyoto, Japan

[21] Appl. No.: 922,059

[22] Filed: Jul. 29, 1992

[30] Foreign Application Priority Data

Jul. 30, 1991 [JP] Japan ................... 3-212845

[51] Int. Cl.$^5$ ............................. G01N 21/00
[52] U.S. Cl. .................... 356/237; 250/236; 250/563; 250/571
[58] Field of Search ............... 356/237, 431; 250/563, 250/561, 572, 236, 571

[56] References Cited

U.S. PATENT DOCUMENTS

| | | | |
|---|---|---|---|
| 4,468,120 | 8/1984 | Tanimoto et al. | 356/237 |
| 4,610,541 | 9/1986 | Tanimoto et al. | 356/237 |
| 4,829,175 | 5/1989 | Goto et al. | 250/236 |
| 4,889,998 | 12/1989 | Hayano et al. | 250/563 |
| 4,898,471 | 2/1990 | Stonestrom et al. | 356/237 |
| 4,902,131 | 2/1990 | Yamazaki et al. | 356/237 |
| 4,999,510 | 3/1991 | Hayano et al. | 250/571 |

*Primary Examiner*—Robert J. Warden
*Assistant Examiner*—Hien Tran
*Attorney, Agent, or Firm*—Price, Gess & Ubell

[57] ABSTRACT

A laser beam particle-detecting apparatus can automatically detect the position of minute particles on a substrate. A laser beam can be scanned across the substrate, and optical detectors can optically detect the laser beam after incidence with the substrate to define the position of any minute particles. Correction factors characteristic of the laser beam particle-detecting apparatus can be utilized to adjust the coordinates of the particle position, whereby any inaccuracies in the detecting apparatus can be compensated.

5 Claims, 6 Drawing Sheets

OPTICAL DETECTING SYSTEM WITH SELF-CORRECTION

BACKGROUND OF THE INVENTION

1. Field of the Invention

The present invention relates to an apparatus for detecting particles that may be stuck on the surfaces of substrates, for example, reticles and masks used for producing printed circuit patterns on semiconductor wafers or substrates that are used in liquid crystal displays and, more particularly, to a self-correcting or calibrating feature which can compensate for any errors in the detecting apparatus.

2. Description of Related Art

An apparatus for detecting particles in which an inspection stage receives a substrate to be inspected is known. An inspection stage is adapted to linearly move between a particle-detecting position or station and a subsequent particle observing position or station. In the particle-detecting position, a laser beam is applied at a predetermined angle to the surface of the substrate. The laser beam can have a polarized characteristic and can be scanned across the substrate by a revolving beam-scanning mirror. Any reflected and/or scattered incident laser beams that have been reflected or scattered from the particles and the like on the surface of the substrate will be detected by a detector optical system that is positioned adjacent to the substrate and is capable of recording variations in the intensity of reflected or scattered laser beams. The existence of a minute particle on the substrate surface can have the characteristic of reflecting and scattering the laser beam, and will vary the intensity of the detected signal from the detector optical system to indicate a measurement of the size of the particle, and also the position of the particle on the substrate. The substrate can then be moved to the particle observing position, and a correlation between the detected positions of the particles can be used to align the substrate for visual observation and confirmation by the operator with the use of a microscope. Thus, minute particles can be efficiently observed if accurate particle positioning information can be provided.

In the operation of the conventional apparatus for detecting particles, there is a relationship between the angle of the swing signal of the beam-scanning mirror that reciprocally scans a laser beam, emitted from a laser cavity, and an angle of swing or position of a laser beam spot on the substrate, which is calculated on the basis of the angle of the swing signal from the beam-scanning mirror. Thus, the position of the laser beam is determined during the scan cycle.

However, there is a possibility that the laser beam as incident upon the substrate to be inspected may be in disagreement with the angle of the swing signal output from the beam-scanning mirror. Thus, the beam spot, due to characteristics of the actual optical detecting system such as the optical adjustment of the incident optical system and the accuracy of the optical elements, along with alignment features of the components, can produce an error between an apparent detected position and an actual position which requires realignment and readjustments of the microscope to hunt for the detected particle.

Referring to FIG. 5, this error is graphically disclosed. If there are no errors in the optical detecting system and it performed hypothetically in accordance with its design purpose, then a linear relationship would be maintained between the detected position and actual position of any minute particles, such as shown by the straight line I in FIG. 5. The line II discloses, in fact, the detected positions that the apparatus provides as a result of the various inaccuracies that are inherent in a production line optical detecting system.

SUMMARY OF THE INVENTION

The present invention addresses the problems of the above prior art by providing an optical detecting system wherein the detection of particles can be compensated for any inaccuracies inherent in the optical detecting system. Thus, the output signal from the optical detecting system can be adjusted or corrected to accurately provide the position of any minute particles or foreign substances on a substrate to be inspected.

The present invention determines a certain functional relationship (spline function) for a plurality of particles on the basis of actual positional information of particles based on the angle of the swing signals of a beam-scanning mirror and movemental information in a scanning direction of an inspection stage to correct detected positions of particles on the basis of this predetermined functional relationship. As a result, the detected positions of a plurality of particles can be plotted to obtain the functional relationship between the angle of swing signals of the beam-scanning mirror and the actual positional information of the particles, whereby the output signals can be accurately adjusted to define the actual position of the particles on the substrate to be inspected.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved optical detector with stored correction factors.

Figure 1:
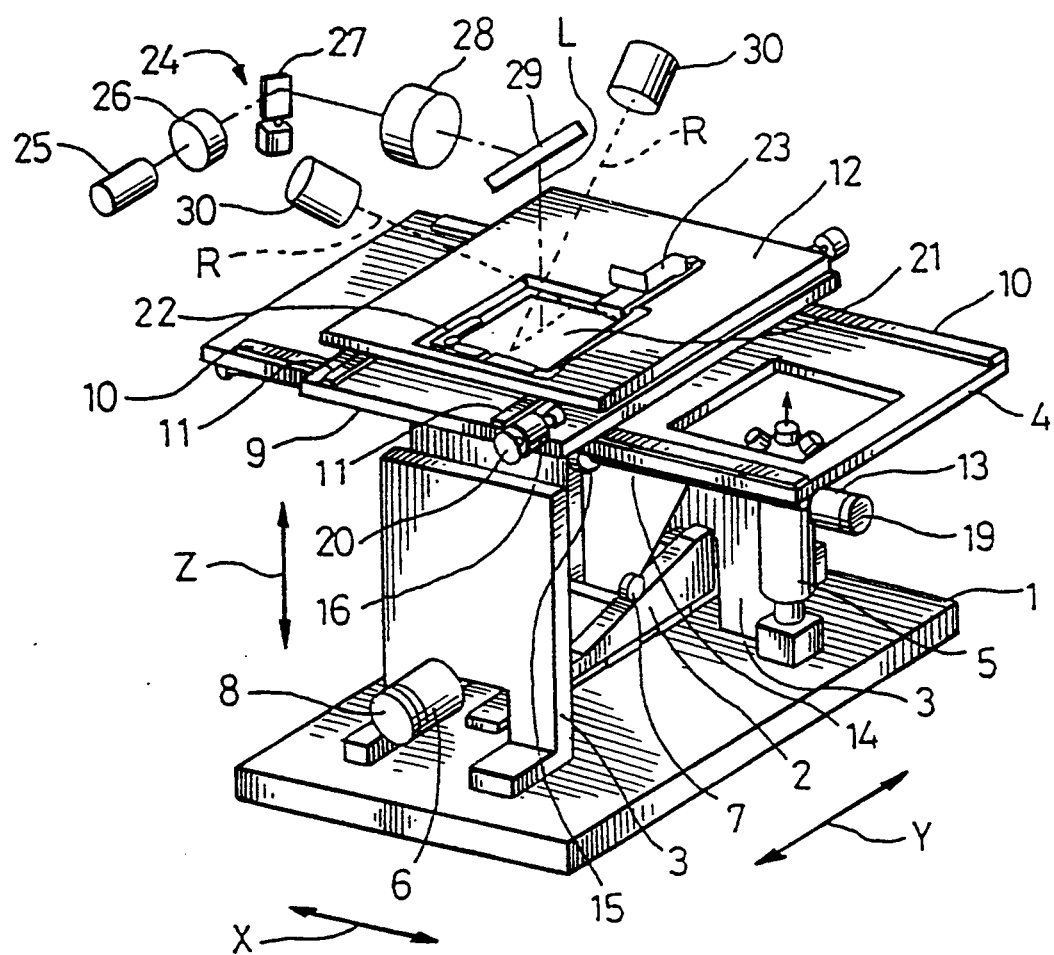
FIG. 1 is a perspective schematic view showing the main component parts of an optical-detecting apparatus for detecting particles in accordance with the present invention.
Figure 2:
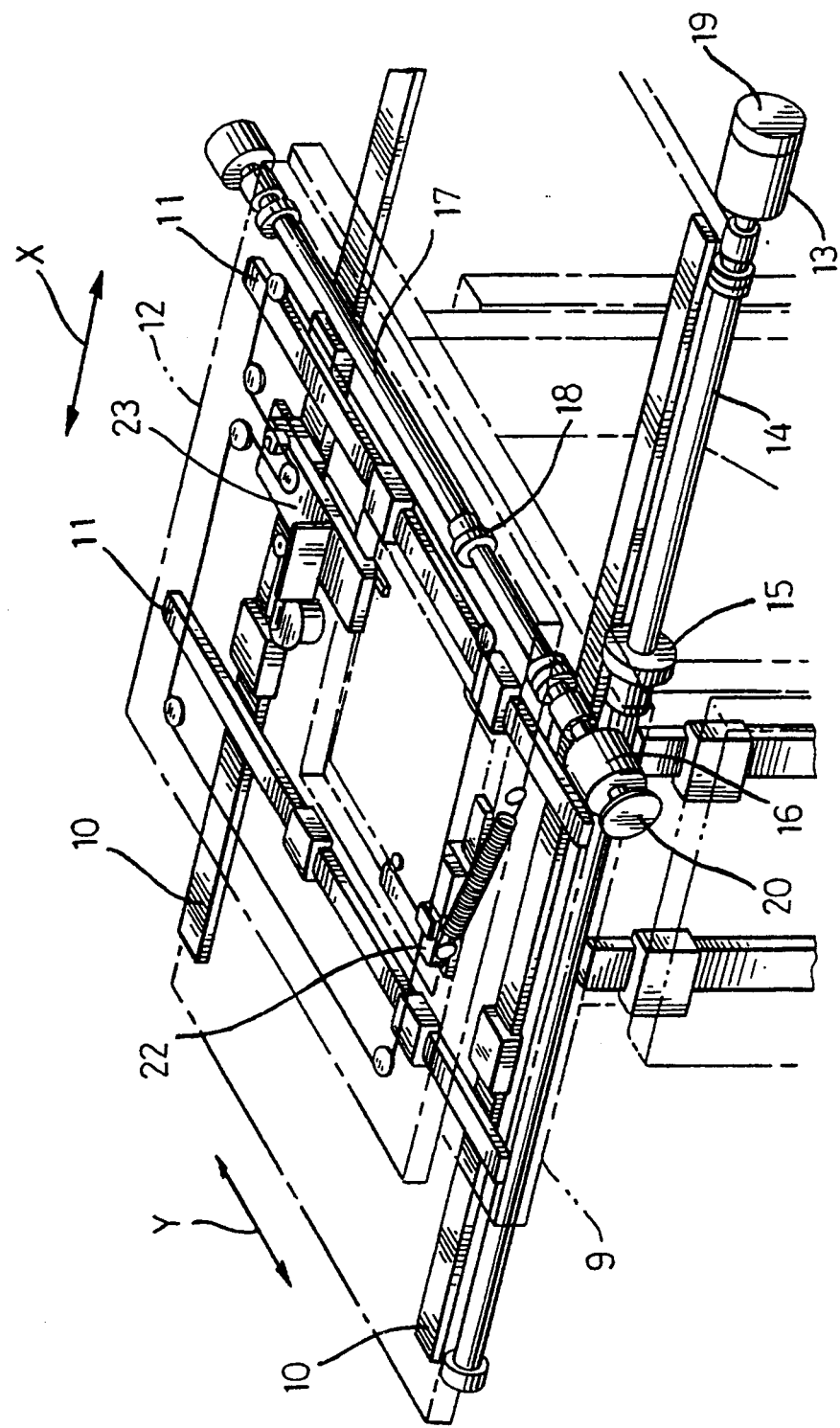
FIG. 2 is a partial perspective view disclosing a driving system for the optical detecting apparatus.

Referring to FIGS. 1 and 2, a fixed base 1 is provided with a trestle 4 elevated in the vertical direction Z (up and down direction) by a support or standing member 3. Cam 2 can provide relative motion in the direction of Y (the back and forth direction). A microscope 5 is mounted on the base member 1 to provide a visual inspection station. The fixed base 1 is further provided with a threaded shaft (not shown) that is connected with a pulse motor 6 at one end and aligned in the direction of Y. The cam 2 is provided with a corresponding threaded nut member (not shown) that engages with the threaded shaft so that a cam follower 7 can be pivotally mounted on the cam 2 below the trestle 4. A rotary encoder 8 can be provided in the vicinity of the pulse motor 6 to monitor the movement and to provide signals to a control circuit such as a microprocessor-based system.

A slide base 9 is driven in the direction of X (the right and left direction) along a guide rail 10 which is mounted on the upper surface of the trestle 4. The particle inspection station 12 can be driven in the direction of Y along the guide rail 11 across the upper surface of the slide base 9. The inspection station 12 is movable between the particle-detecting position and a particle-observing position as a result of movement of the slide base 9.

Figure 3:
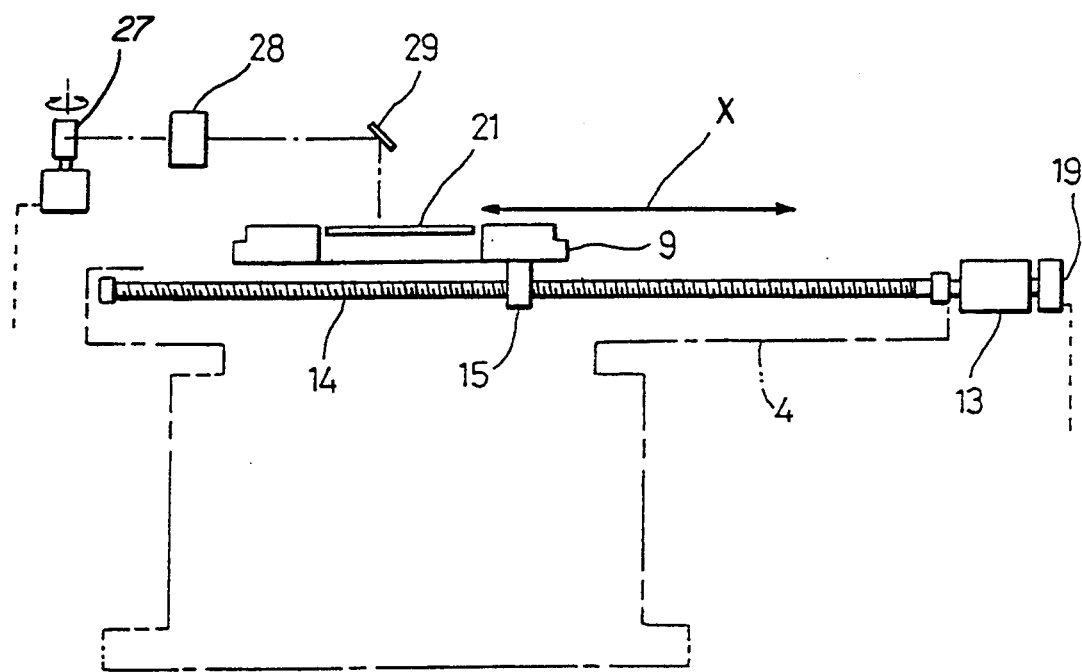
FIG. 3 is an elevated schematical view showing component parts of the driving system in the direction of X.
Figure 4:
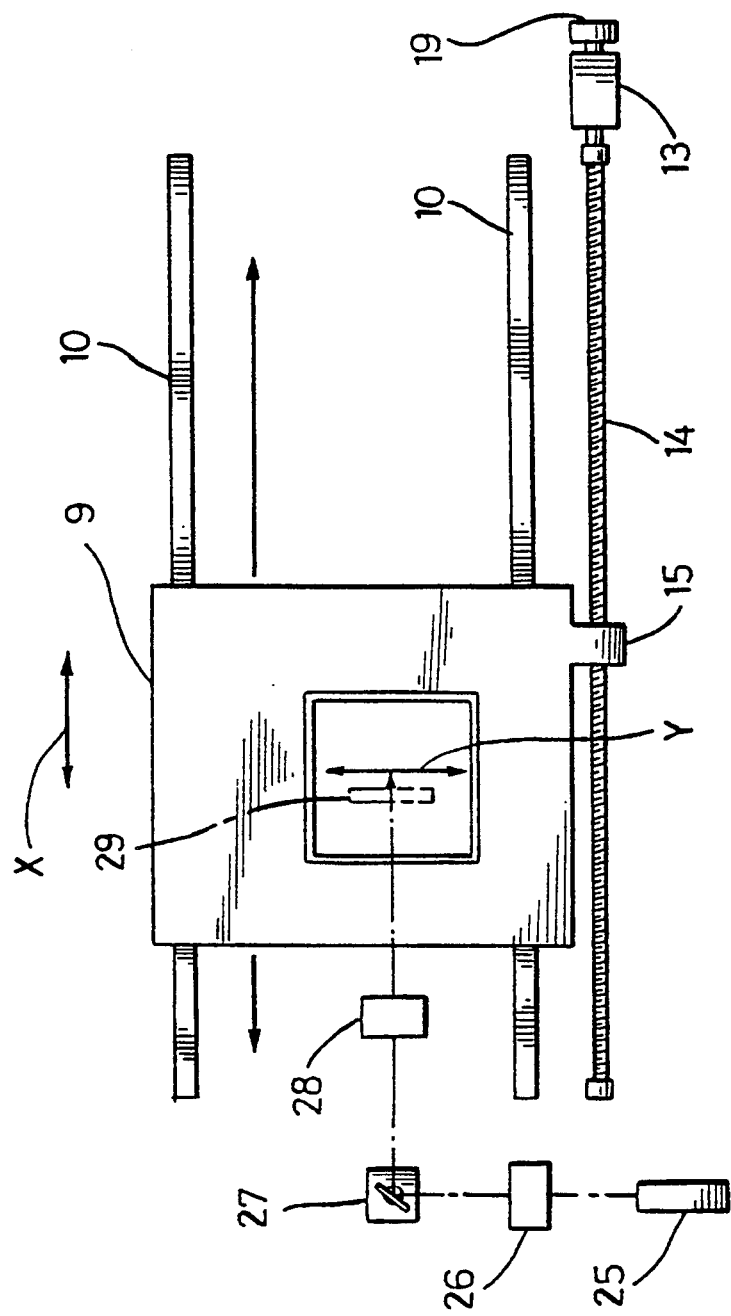
FIG. 4 is a plan partial view showing component parts of the driving system in the direction of X.

As shown in FIGS. 3 and 4, a threaded shaft 14, which is connected with a pulse motor 13 at one end thereof, is aligned in the direction of X on the trestle 4. A nut member 15 with appropriate threads is engaged with the threaded shaft 14 and provided on the slide base 9.

In addition, a nut member 18, which is connected with a pulse motor 16 at one end thereof, is further engaged with a threaded shaft 17 extended in the direction of Y. The nut member 18 is provided on a lower surface of the inspection stage 12. Rotary encoder 19 and 20 are provided in the vicinity of the pulse motors 13 and 16, respectively. A fixed member 22 and a movable member 23 are provided on an upper surface of the inspection stage 12 for mounting and fixing a substrate 21 to be inspected, such as reticles, that are used for printing a circuit pattern on a semiconductor wafer at predetermined positions.

Referring to FIG. 1, the incident optical system 24 for providing the scanning laser beam includes an He-Ne laser cavity 25 for generating a laser beam L having an appointed angle of polarization. A beam expander 26 is positioned adjacent to the cavity 25 and before a beam-scanning mirror 27. The beam-scanning mirror 27 can rotate to scan the laser beam in the direction of Y after contacting a collecting lens 28 and an inclined mirror 29. Thus the laser beam will scan across an inspection line in a vertical position downward on a substrate 21. A pair of detector optical systems 30 are arranged at suitable positions in an inclined upper portion in the direction of Y and include a collecting lens, a slit, and an analyzer for cutting a specific straight polarized component with an optical detector arranged for receiving the light. The individual components are not disclosed herein. These optical detectors, which are mounted on either side of the inclined mirror 29, are capable of detecting the reflected and scattered beams R produced from the laser beam L as incident upon the substrate to be inspected.

In operation, a substrate 21 which is to be inspected is placed on the inspection stage 12 at the particle-detecting position. The laser beam L, having an appointed or predetermined angle of polarization, is scanned to be incident upon the surface of the substrate 21 by means of the beam-scanning mirror 27 as the substrate is relatively advanced after each scan angle. The reflected and scattered beams R are detected from the surface of the substrate 21 when they are incident upon the detecting optical systems 30. The existence of minute particles on the surface of the substrate 21 is accordingly detected, and their sizes can be further measured on the basis of the results of the detection of the reflected and scattered beams R. The substrate 21 can then be moved to a particle-observing position, where the previously-detected minute particles can be magnified by means of a microscope 5 for an observer to confirm their existence and their impact upon the part.

In order to magnify these particles, the inspection stage 12 with the substrate 21 mounted thereon should be moved to the particle-observing position adjacent to the microscope 5 based on the actual positional information of the detected particles, so that the observer can immediately ascertain their position and nature. This movement is based upon the actual positional data that is processed, for example, by a computer-based circuit, from the outputs of the optical detectors 30 and the swing angle or position of the scanning laser beam L. Such information or data of the actual detected positional coordinates of minute particles can be plotted, as shown by the marks x in FIG. 5. These positions are determined on the basis of the quantities of movement in the scanning direction of the inspection stage 12 along the direction shown by both arrows X in FIGS. 3 and 4 and, as can be seen, disclose a curved relationship relative to the theoretical straight line position of line I which would represent an idealized system. The functional relationship between the detected particles has been defined as a spline function.

This functional relationship is determined depending upon the specific characteristics of an optical-detecting apparatus. Once this relationship has been determined, for example, by empirical means, then the detected particle positions that are monitored can be appropriately calibrated or corrected so that the positional information can be accurately reproduced and the detected particles can be magnified in an efficient and accurate manner in the inspection stage. In determining a specific spline function for an instrument, it is preferable that the position of the particles to be plotted be selected over a wide range on a substrate to minimize any potential errors.

Figure 5:
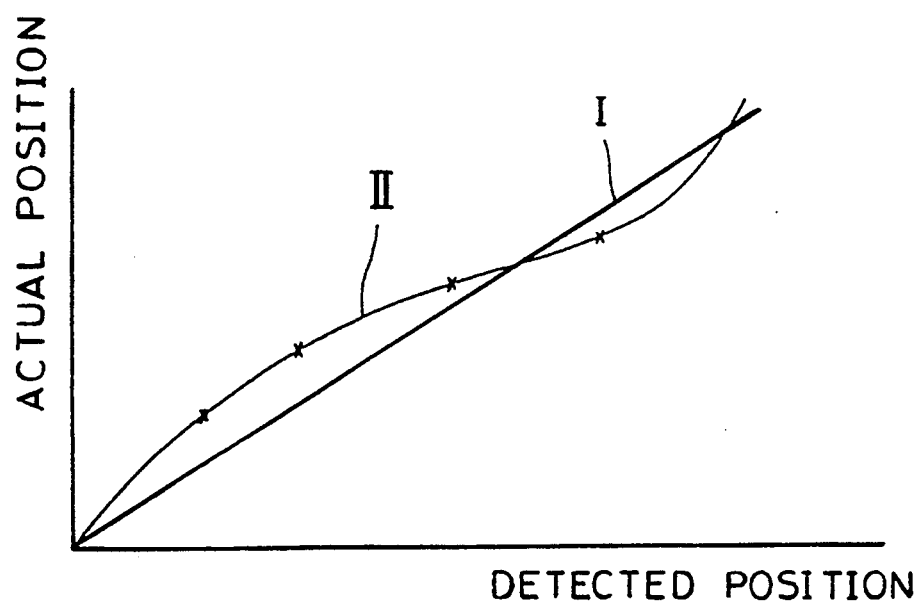
FIG. 5 is a graph disclosing the relationship between the theoretical relationship of detected position and actual positions of minute particles and the actual positions detected as a result of inherent inaccuracies in the optical detecting system.

For example, a test substrate can be utilized having accurately-determined particle positions across its substrate. Since these particle positions have been predetermined, an optical-detecting apparatus without any flaws or technical inaccuracies, such as in the optical system scanning mirror, etc., would reproduce the detected positions of these minute particles consistent with the straight line I, as shown in FIG. 5. Line II, however, indicates a characteristic detection, for example, across one scan cycle of the substrate.

Figure 6:
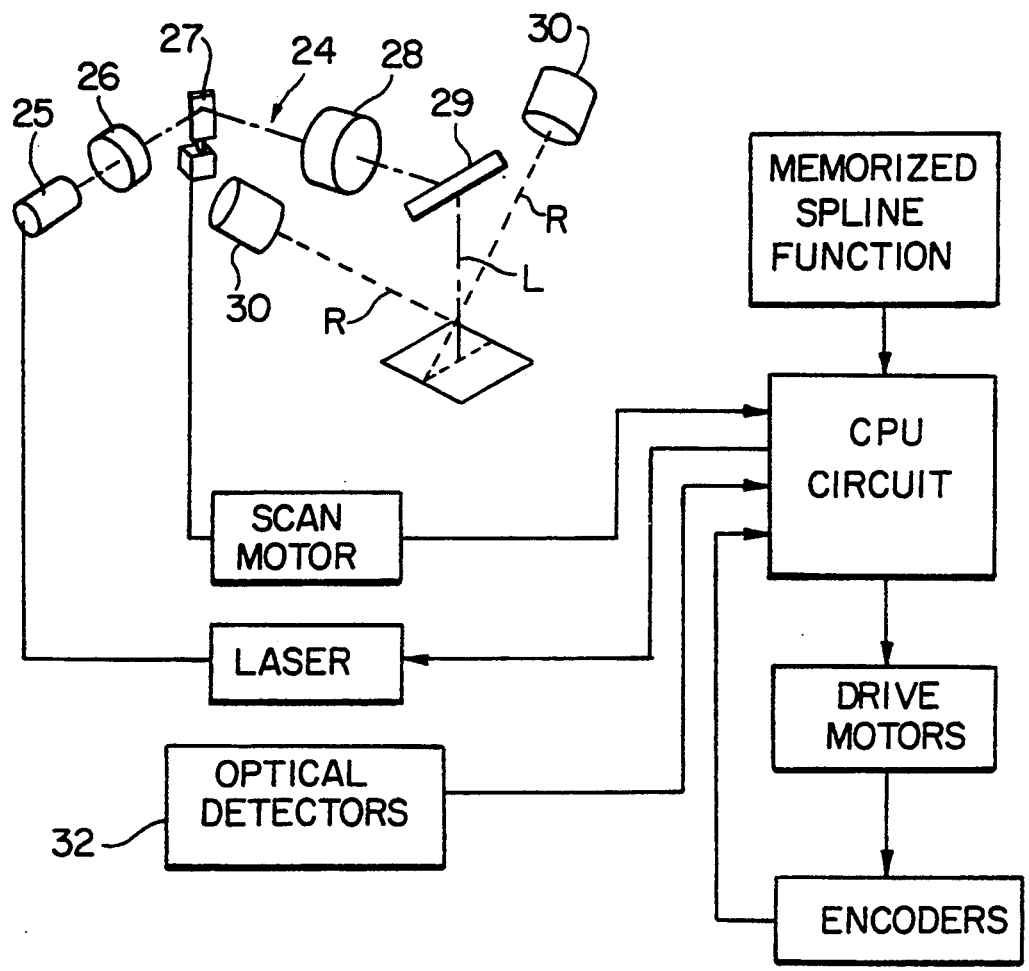
FIG. 6 is a schematic of the control circuit.

The deviations of curve II relative to curve I comprises the functional relationship or spline function characteristic of the apparatus. The coordinates of this deviation can be empirically recorded, for example, in a microprocessor-based memory, during an initial calibration of the optical-detecting apparatus at the factory with a standard test substrate with known particle positions, or by a technician at a customer facility. This data can then be used as correctional data which will provide a correctional coefficient related to the scan angle, as shown in FIG. 6. In the actual operation of the inspection of a substrate with unknown locations of minute particles, the detection of a particle can then be appropriately corrected based on this spline function by a computer circuit, to define the actual physical coordinates of the minute particle in an output signal that can be used to adjust the position of the substrate 21 accurately over the microscope 5.

As can be readily appreciated, a microprocessor-based or computer-based system storing these correctional coefficients can process inputs of the scan angle and the inputs of the detector optical systems 30 to determine initial positions of the detected minute particles. These coordinate positions can then be appropriately corrected based on the stored spline function data in an automatic process by the computer control circuit in a known programming exercise.

In accordance with the present invention, the detected positions of the detected particles are correctly and accurately reproduced so that these positions can be inspected even though there may be an inherent disagreement between the angle of the swing signals that is output from the beam-scanning mirror and the actual laser beam spot due to the spline function of the optical apparatus.

As can be readily appreciated, some of these errors, such as the optical adjustment and the incident optical system for scanningly applying the laser beam to the substrate, and the accuracy of optical elements, do not necessarily change over a period of time. The initial calibration of these spline functions can be more efficient than attempting to maintain tighter tolerance and component specifications for these components.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A particle-detecting apparatus for particles on an object comprising:
   means for scanning an object with a light beam along discrete scan lines;
   means for detecting light from the scanned light beam after incidence with the object;
   means for determining any variation in detected light from said means for detecting light indicative of particles on the object to determine the existence of a particle and detect a particle position;
   means for providing a correction factor that relates the detected particle position to an actual particle position by using a test substrate with predetermined particle positions; and
   means for modifying the detected particle position relationship based on the provided correction factor.

2. In a particle-detecting apparatus for determining the position of minute particles on a substrate having a laser beam scanning across the substrate in an optical path and moving relative to the substrate and detector means for sensing laser light after incidence on the substrate to enable the determination of any particle position, the improvement comprising:
   compensation means including a determination of a correction factor that relates the determined particle position to an actual particle position by determining the positions of particles on a substrate having known particle positions, thereby providing compensation to ensure an accurate determination of the position of any minute particle.

3. The invention of claim 2 wherein the compensation means includes a memory for storing correction coordinates corresponding to the laser beam scanning optical path and a computer circuit for applying the correction coordinates to the particle position.

4. A laser beam particle-detecting apparatus for analyzing substrates to automatically detect the position of minute particles on a semiconductor substrate to enable a subsequent visual inspection, comprising:
   means for supporting a substrate;
   means for scanning a laser beam in a predetermined optical scan path across the substrate including a scanning mirror for directing the scanning laser beam at an acute angle to a surface of the substrate;
   detecting means for optically detecting the laser beam after incidence with the substrate including optical detectors positioned adjacent to the substrate and on either side of the means for scanning, to determine a position of a particle; and
   compensation means for correcting the determined particle position by using correction factors derived by analyzing substrates having particles with known positions.

5. The invention of claim 4, wherein the means for scanning and the detecting means includes optical lens elements, and the compensation means incorporates correction factors that adjust for any inaccuracy of the lens elements.

* * * * *